United States Patent [19]

Bibby et al.

[11] Patent Number: 4,663,969

[45] Date of Patent: May 12, 1987

[54] MEASURING WATER VAPOR TRANSMISSION THROUGH MATERIALS

[75] Inventors: Noel Bibby, Bridgford; John Owens, Bacup Rossendale, both of England

[73] Assignee: Noel Bibby Limited, Nottingham, England

[21] Appl. No.: 767,961

[22] Filed: Aug. 21, 1985

[30] Foreign Application Priority Data

Aug. 22, 1984 [GB] United Kingdom ............... 8421295
Nov. 10, 1984 [GB] United Kingdom ............... 8428481

[51] Int. Cl.$^4$ .......................................... G01N 15/08
[52] U.S. Cl. ........................................ 73/159; 73/38; 324/439
[58] Field of Search ............... 374/5, 4; 73/159, 73, 73/75, 76, 38; 210/96.1; 436/3, 5, 150, 178; 340/601, 602, 605; 324/439, 450, 441; 8/149.3

[56] References Cited

U.S. PATENT DOCUMENTS

| | | | |
|---|---|---|---|
| 2,347,661 | 5/1944 | Butland | 73/159 |
| 2,400,481 | 5/1946 | Brabender | 73/159 |
| 2,904,996 | 9/1959 | Lamb et al. | 73/38 |
| 2,913,386 | 11/1959 | Clark, Jr. | 324/439 |
| 3,266,306 | 8/1966 | Arnold et al. | 73/159 |
| 3,286,509 | 11/1966 | Glickman et al. | 73/38 |
| 3,580,067 | 5/1971 | Mandrell | 73/159 |
| 3,590,634 | 7/1971 | Pasternak | 73/38 |
| 3,604,246 | 9/1971 | Toren | 73/38 |
| 3,760,773 | 9/1973 | Christensen | 73/38 |
| 4,050,995 | 9/1977 | Bredewer | 73/76 |

FOREIGN PATENT DOCUMENTS

| | | | |
|---|---|---|---|
| 0079236 | 6/1981 | Japan | 73/38 |
| 0176539 | 10/1983 | Japan | 324/450 |
| 0655939 | 4/1979 | U.S.S.R. | 73/38 |
| 0775669 | 10/1980 | U.S.S.R. | 73/38 |
| 1138711 | 2/1985 | U.S.S.R. | 73/38 |

OTHER PUBLICATIONS

Honewells New Electronic "WVT" Water Vapor Transmission Rate Tester for Packaging Materials, Minneapolis, Minn., 4/66.

Primary Examiner—Charles Frankfort
Assistant Examiner—Thomas B. Will
Attorney, Agent, or Firm—Cohn, Powell & Hind

[57] ABSTRACT

The method and apparatus for testing the vapor transmission characteristics of a sheet material which comprises disposing said material at an interface between an aqueous solution and a plenum chamber, maintaining the temperature of the solution at a predetermined level, maintaining the temperature and humidity in the plenum chamber at a predetermined level and measuring the chamge in concentration of the solute in the solution over a predetermined period of time.

12 Claims, 1 Drawing Figure

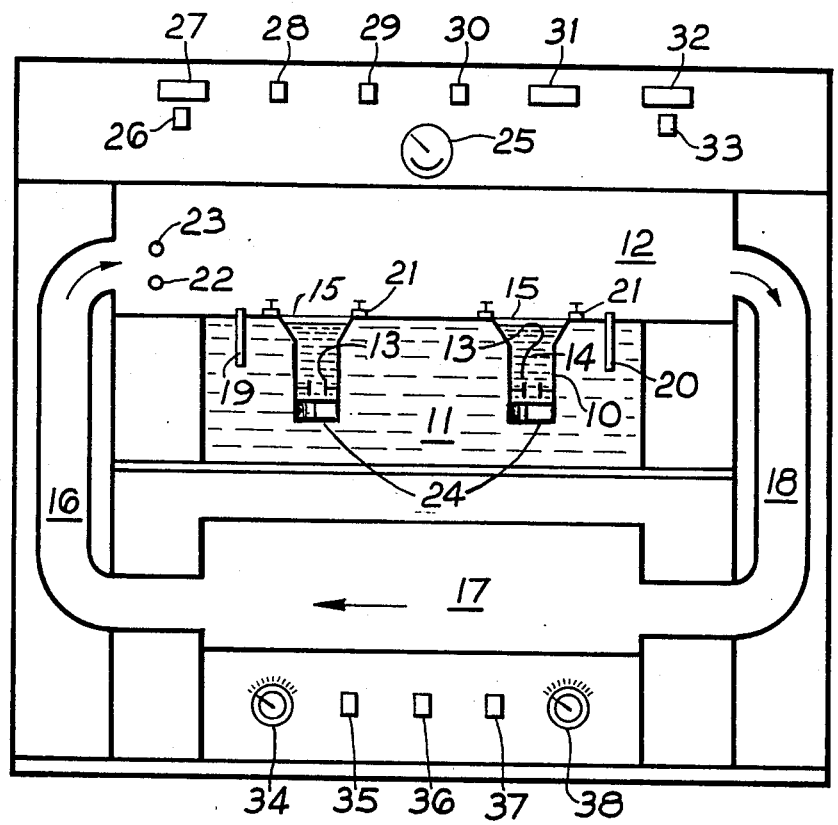

MEASURING WATER VAPOR TRANSMISSION THROUGH MATERIALS

This invention relates to a method and apparatus for measuring water vapour transmission through materials, for example textile fabrics and the like.

One example of a material whose water vapour transmission it may be desirable to measure is garment fabric. Rainproof garments may be made from textile fabrics coated with a layer of proofing material such as a plastics material. With suitable sealing at the seams, for example by welding, these garments can be made completely rainproof. A problem which is experienced, however, is that perspiration cannot escape and this leads to a build-up of moisture inside the garment, particularly when the wearer is engaged in strenuous exercise. Various proposals have been made for improving the vapour transmissibility of the fabric while retaining its rainproof characteristics, but there is a need to measure accurately the rate at which vapour is transmitted through the fabric so that comparisons may be made between different types of fabric.

Attempts have been made to measure water vapour transmission by using the change in weight of dessicants in a container closed by a sample of the fabric, whose other face is exposed to a humid atmosphere, e.g. in a heated chamber containing water. It is desirable to measure vapour transmission over a long period, for example 24 hours, to give a vapour transmission measurement which can be readily related to use of the fabric in a garment. However, water absorption by dessicants gives rise to localised saturation which reduces the efficiency of water absorption, and so over a 24 hour period, the rate of water absorption will vary considerably. Thus, any measurement of water vapour transmission through the fabric will be inaccurate, and the inaccuracy is magnified when the rate is expressed in terms of a square meter of the fabric. Additionally, a dessicant will need to be removed from the test apparatus for weighing, and during weighing, both initially and finally, it may be subjected to an environment having a different moisture content, which can affect the accuracy of the weighing. In addition, weighing small samples of dessicant accurately is difficult and the change in weight over a 24 hour period may be relatively small, with the result that the water vapor transmission figure derived is even less accurate. Finally, a variation of initial conditions inside the chamber containing the dessicant will again affect the accuracy of the figure obtained.

An object of the present invention is to provide an improved and reliable means for measuring the vapour transmission of a sheet material. A further object is to provide a standard test procedure which will enable users to compare the vapour transmission characteristics of sheet materials.

According to one aspect of the present invention we provide apparatus for testing the vapour transmission characteristics of a sheet material comprising an open-topped test chamber for receiving an aqueous solution, means for measuring the change in concentration of the solute in the solution and means for securing said sheet material adjacent said open top of said test chamber.

Preferably said apparatus includes a heating chamber in which said test chamber is located and a plenum chamber located above said open top of said test chamber. The heating chamber may be a water bath with a thermostatically controlled heating means.

The plenum chamber is preferably connected to an air conditioning unit.

In one embodiment of the invention the means for measuring the change in concentration of the solute in the solution is conductivity measuring means.

In order to avoid inconsistent readings due to vapour transmission across a gap between the surface of the aqueous solution and the sheet material it is desirable to include means for maintaining the level of solution in the test chamber.

According to another aspect of the invention we provide a method of testing the vapour transmission characteristics of a sheet material which comprises disposing said material at an interface between an aqueous solution and a plenum chamber, maintaining the temperature of the solution at a predetermined level, maintaining the temperature and humidity in the plenum chamber at a predetermined level and measuring the change in concentration of the solute in the solution over a predetermined period of time.

Preferably the solution is an electrolyte and the change in concentration is measured by measuring the change in conductivity of the solution. The means for measuring the conductivity may comprise a pair of electrodes within the electrolyte and conductivity measuring apparatus, for example a conductivity bridge, connected thereto.

Preferably, where garment fabrics and the like are to be tested, the electrolyte is a saline solution maintained at approximately blood temperature, so as closely to simulate human perspiration.

It is envisaged that standardised test conditions could be defined to give a comparative water vapour transmission rating for fabrics. The term "fabric" used herein includes textile and non-textile fabrics, both with and without proofing coatings, films and foils.

Reference is now made to the drawing, which shows diagrammatically an apparatus in accordance with the invention.

The apparatus comprises a cabinet which incorporates a heating chamber in the form of a water bath 11. The bath 11 is provided with heating means 20 which is controlled by a thermostat 19.

Two test chambers 10 are provided, each being adapted to receive an aqueous solution, such as a saline solution, providing an electrolyte 14 and being provided with a pair of electrodes 13. Each pair of electrodes is connected into an electrical bridge circuit (not shown) of a conductivity measuring means which includes a digital readout (27 and 32 respectively) each associated with a readout on/off switch (26 and 33 respectively). The electrical bridge circuit should use an AC supply to avoid electrolysis of the electrolyte.

Each test chamber 10 is associated with clamping rings 21 which enable a test disc 15 of sheet material to be clamped over the mouth of the test chamber above the level of the electrolyte 14.

Above the test chambers on the opposite side of the test discs when in position there is provided a plenum chamber 12 supplied with air from an air conditioning unit 17 by way of one or more ducts 16, the air being returned to the conditioning unit by way of one or more ducts 18.

The air conditioning unit is provided with conventional elements (not shown) for controlling temperature and humidity of the air in response to outputs from temperature probe 22 and humidity probe 23. The conditioning unit control panel includes temperature and humidity setting indicators 34 and 38 respectively and on/off switches for controlling heat (35) refrigeration (36) and humidity (37).

The control panel for the heating tank comprises an an/off mains switch 28, tank boost heat on/off switch 29, tank heat on/off switch 30 and a tank temperature digital readout 31. The cabinet temperature and humidity are shown on indicator 25.

In use, the apparatus is calibrated using solutions of known concentration in the test chamber, and then the standard test solution is introduced. Under standard test conditions, the starting solution will be specified. A sample of the fabric to be tested is clamped to the open top of the test chamber by the clamping ring 21, the conditions in the plenum chamber 12 adjusted to simulate a specified environment and the temperature of the solution allowed to reach the temperature of the water tank. The change in conductivity of the test solution is then measured over a test period of, for example, 24 hours. From the overall change in conductivity of the test solution, the total weight of water lost from the solution can be calculated and this can be expressed as a weight per square meter of the fabric, the exposed area of the fabric being known from the dimensions of the open top of the test chamber. Alternatively, it may be possible to calibrate the conductivity meter in terms of weight loss per square meter of test sample, to give a direct measurement after any desired time interval.

Using the apparatus and method of the invention, accurate comparisons may be made of the water vapour transmission of materials such as fabrics under a wide range of conditions, thus assisting not only the development of improved fabrics, but also providing a standard to enable potential purchasers to assess the comfort of the garment from a quoted test figure. In addition to fabrics for garments, fabrics for use in applications such as sleeping bags and tents may also be tested. Further, the apparatus and method of the invention may be used in the measurement of water vapour transmission through a wide range of materials other than fabrics, for example, electrical installation materials, damp-proof membranes for building purposes, and paints and varnishes. The invention is particularly applicable to measurement of water vapour transmission through relatively thin materials.

In certain circumstances, the accuracy of reproducability of the measurements obtained may be adversely affected by the change in level of the saline solution 14 as it evaporates during the course of the test. This can give rise to a gradual increase in the resistance to movement of the water vapour across the air gap above the saline solution as the level drops.

Accordingly where greater accuracy and consistency of measurement over a period of time is required, level adjusting means may be provided to ensure that the level is kept constant throughout the test. There are a number of ways in which this can be achieved. For example, the base of the chamber 10 may be formed as a sealed movable piston 24 which is moved upwardly at a rate sufficient to compensate for the fall in saline solution level.

Other suitable means for keeping the level constant include a flexible diaphragm in the wall of the chamber 10, with means for expanding the diaphragm mechanically, hydraulically or pneumatically to change the volume of the chamber as required, or provision of means for the addition of saline solution at a rate sufficient to equal the rate of evaporation. In the latter case, the conductivity measurement would require suitable correction.

The level can be monitored by any suitable means, for example a float operated electrical level switch, or a photoelectric device and the output from the device utilized to control the level adjusting means.

We claim:
1. Apparatus for testing the vapor transmission characteristics of a sheet material comprising an open-topped test chamber for receiving an aqueous solution containing a solute, means for measuring a change in concentration of the solute in the solution, sheet material securing means adjacent said open top of said test chamber such that said sheet material substantially completely covers said open top of said test chamber, a heating chamber in which said test chamber is located and a plenum chamber located above said open top of said test chamber.

2. Apparatus according to claim 1 in which said heating chamber is a water bath with a thermostatically controlled heating means.

3. Apparatus according to claim 1 in which an air conditioning unit is connected to said plenum chamber.

4. Apparatus according to claim 2 in which an air conditioning unit is connected to said plenum chamber.

5. Apparatus according to claim 1 in which the means for measuring the change in concentration of the solute in the solution is conductivity measuring means.

6. Apparatus according to claim 1 including means for maintaining a constant level of solution in the test chamber.

7. Apparatus according to claim 1 in which the means for measuring the change in concentration of the solute in the solution is conductivity measuring means and including means for maintaining a constant level of solution in the test chamber.

8. A method of testing the vapour transmission characteristics of a sheet material which comprises disposing said material at an interface between an aqueous solution containing a solute and a plenum chamber, maintaining the temperature of the solution at a predetermined level, maintaining the temperature and humidity in the plenum chamber at a predetermined level and measuring a change in concentration of the solute in the solution over a predetermined period of time and computing the vapour transmission characteristics from the measurement obtained.

9. A method according to claim 8 in which the solution is an electrolyte and the change in concentration is measured by measuring a change in conductivity of the solution.

10. A method according to claim 9 in which the solution is a saline solution.

11. A method according to claim 8 in which the predetermined temperature is approximately the blood temperature of a living human.

12. Apparatus for testing the vapour transmission characteristics of a sheet material comprising an open-topped test chamber for receiving an aqueous solution containing a solute, means for measuring a change in concentration of the solute in the solution, said means being conductivity measuring means, sheet material securing means adjacent said open top of said test chamber such that said sheet material substantially completely covers said open top of said test chamber, a heating chamber in which said test chamber is located, said heating chamber being a water bath with a thermostatically controlled heating means, a plenum chamber located above said open top of said test chamber, an air conditioning unit connected to said plenum chamber and means for maintaining a constant level of solution in the test chamber.

* * * * *